US007972795B2

(12) United States Patent
Thorin et al.

(10) Patent No.: US 7,972,795 B2
(45) Date of Patent: Jul. 5, 2011

(54) ANGIOPOIETIN-LIKE 2 AS A BIOMARKER OF VASCULAR ENDOTHELIAL CELL ABNORMAL FUNCTION AND SENESCENCE

(75) Inventors: Eric Thorin, Montreal (CA); Nada Farhat, Saint-Laurent (CA); Nathalie Trescases, Montreal (CA)

(73) Assignee: Institut de Cardiologie de Montreal, Montreal, Quebec (CA)

( * ) Notice: Subject to any disclaimer, the term of this patent is extended or adjusted under 35 U.S.C. 154(b) by 664 days.

(21) Appl. No.: 11/812,621

(22) Filed: Jun. 20, 2007

(65) Prior Publication Data
US 2008/0166717 A1 Jul. 10, 2008

Related U.S. Application Data

(60) Provisional application No. 60/814,894, filed on Jun. 20, 2006.

(51) Int. Cl.
*G01N 33/53* (2006.01)
(52) U.S. Cl. .......................................... 435/7.1; 530/350
(58) Field of Classification Search .................. 435/7.1; 530/350
See application file for complete search history.

(56) References Cited

FOREIGN PATENT DOCUMENTS
EP 1 308 511 A1 * 5/2003

OTHER PUBLICATIONS

Lee, KW et al. Plasma angiopoietin-1, angiopoietin-2, angiopoietin receptor Tie-2 and vascular endothelial growth factor levels in acute coronary syndromes. Circulation, vol. 110, pp. 2355-2360, 2004.*
Narayan S, et al. Cigarette Smoke Condensate-Induced Transformation of Normal Human Breast Epithelial Cells in Vitro. Oncogene. Jun. 2004; 23: 5880-9.
Blann AD, Mc Collum CN. Adverse Influence of Cigarette Smoking on the Endothelium. Thromb Haemost. May 1993; 70: 707-711.
Barua RS, Ambrose JA et al. Heavy and Light Cigarette Smokers Have Similar Dysfunction of Endothelial Vasoregulatory Activity. J Am Coll Cardiol. Mar. 2002; 39: 1758-1763.
Celemajer DS,Adams MR, Clarkson P et al., Passive Smoking and Impaired Endothelium-Dependent Arterial Dilatation in Healthy Young Adults. N Engl J Med. Jan. 1996; 334: 150-154.
Ambrose JA, Barua RS. The Pathophysiology of Cigarette Smoking and Cardiovascular Disease. An Update. J Am Coll Cardiol. Dec. 2003; 43: 1731-1737.
Kondo T, Hayashi M et al. Smoking Cessation Rapidly Increases Circulating Progenitor Cells in Peripheral Blood. Arterioscler Thromb Vasc Biol. May 2004; 24: 144.
Moreno H Jr, Chalon S, et al. Endothelial Dysfunction in Human Hand Veins is Rapidly Reversible After Smoking Cessation. Am J Physiol. May 1998; 275: H1040-H1045.
Wannamethee SG et al PH. Associations Between Cigarette Smoking, Pipe/Cigar Smoking, and Smoking Cessation. Eur Heart J. Apr. 2005; 26: 1765-1773.

Yanbaeva DG, Dentener MA, Creutzberg EC, Wesseling G, Wouters EF. Systemic Effects of Smoking. Chest. Oct. 2007; 131: 1557-66.
Heitzer T, Just H, Munzel T. Antioxidant Vitamin C Improves Endothelial Dysfunction in Chronic Smokers. Circulation. May 1996; 94: 6-9.
Barua RS, Ambrose JA et al. Reactive Oxygen Species Are Involved in Smoking-Induced Dysfunction of Nitric-Oxide Biosynthesis. Circulation. Apr. 2003; 107: 2342-2347.
Chen J, Goligorsky MS. Premature Senescence of Endothelial Cells: Methusaleh's Dilemma. Am J Physiol. May 2006; 290: H1729-H173.
Ben-Porath I, Weinberg RA. The Signals and Pathways Activating Cellular Senescence. Int J Biochem Cell Biol. Oct. 2004; 37: 961-976.
Wagner M, Hampel B et al. Replicative Senescence of Human Endothelial Cells in Vitro Involves G1 Arrest. Exp Gerontol. Mar. 2001; 36: 1327-1347.
Benetos A, Okuda K et al. Telomere Length as an Indicator of Biological Aging: The Gender Effect and Relation . Hypertension. Dec. 2000; 37: 381-385.Serrano A.
Cohen RA. The Role of Nitric Oxide and Other Endothelium-Derived Vasoactive Substances in Vascular Disease. Prog Cardiovasc Dis. Sep. 1995; 38: 105-128.
Serrano AL, Andres V. Telomeres and Cardiovascular Disease: Does Size Matter? Circ Res. Feb. 2004; 94: 575-584.
Allsopp RC, Chang E. et al. Telomere Shortening in Associated With Cell Division in Vitro and in Vivo. Exp Cell Res. Jun. 1995; 200: 194-220.
Toussaint O, Medrano EE, Von Zglinicki T. Cellular and Molecular Mechanisms of Stress-Induced Premature Senescence (SIPS). Exp Gerontol. Jul. 2000; 35: 927-945.
Shi W, Haberland ME, Jien ML, Shih DM, Lusis AJ. Endothelial Responses to Oxidized Lipoproteins Determine Genetic. Circulation. Feb. 2000; 102: 75-81.
Thorin E, Shatos MA, Shreeve SM, Walters CL, Bevan JA. Human Vascular Endothelium Heterogeneity. A Comparative .Endothelial Cells. Stroke. Oct. 1996; 28: 375-381.
Dimri GP, et al. A Biomarker That Identifies Senescent Human Cells in Culture and in Aging Skin in Vivo. Proc Natl Acad Sci USA.Sep. 1995; 92: 9363-9367.
Wang P, Zhang Z, Ma X, Huang Y, Liu X, Tu P, Tong T. HDTIC-1 and HDTIC-2, Two Compounds Extracted From Astragali Radix, Mech Ageing Dev. Aug. 2003; 124: 1025-1034.
Hatsuda S, Shoji T, Shinohara K, Kimoto K, Mori K, Fukumoto S, Koyama H, Emoto M, Nishizawa Y. Association Between Plasma. J Vas Res. Dec. 2006; 44: 61.

(Continued)

*Primary Examiner* — Prabha Chunduru
(74) *Attorney, Agent, or Firm* — Holland & Hart, LLP

(57) ABSTRACT

A method for assessing a physiological state of a mammal. The method includes: obtaining from the mammal a biological sample; measuring the expression of angiopoietin-like 2 in the biological sample; and assessing the physiological state of the mammal by comparing the measured expression of the angiopoietin-like 2 to a predetermined normal expression level in normal subjects, wherein an increase in angiopoietin-like 2 level over the predetermined normal expression level indicates an abnormal physiological state.

16 Claims, 5 Drawing Sheets

OTHER PUBLICATIONS

Sun H, Zheng J, Chen S, Zeng C, Liu Z, Li L, Enhanced Expression of ANGPTL2 in the Microvascular Lesions. Nephron Exp Nephrol. Mar. 2007; 105: E117-E123.

Galbiati F, Volonte D, Liu J, Capozza F, Frank PG, Zhu L, Pestell RG, Lisanti MP. Caveolin-1 Expression Negatively Regulates Cell Cycle. Mol Biol Cell. Apr. 2001; 12: 2229-44.

Herbig U, et al. Telomere Shortening Triggers Senescence of Human Cells Through a Pathway Involving ATM, P53, and P21 but Not P16INK4A. Mol Cell. May 2004; 14: 501-513.

Pandita TK. ATM Function and Telomere Stability. Oncogene. Jan. 2002; 21: 611-618.

Miyauchi H, Minamino T, Tateno K, Kunieda T, Toko H, Komuro I. AKT Negatively Regulates the in Vitro Lifespan of Human Endothelial Cells. EMBO J. Jan. 2004; 23: 212-220.

Minamino T, Miyauchi H, Tateno K, Kunieda T, Komuro I. AKT-Induced Cellular Senescence. Implication for Human Disease. Cell Cycle. Feb. 2004; 3: 449-451.

Morisada T, Kubota Y, Urano T, Suda T, Oike Y. Angiopoietins and Angiopoietin-like Proteins in Angiogenesis. Endothelium. May 2006; 13: 71-79.

Rytila P, Rehn T, Ilumets H, Rouhos A, Sovijarvi A, Myllarniemi M, Kinnula VL. Increased Oxidative Stress in Asymptomatic Current Chronic. Respir Res. Apr. 2006; 7: 69-79.

Kanazawa H, Asai K, Nomura S. Vascular Endothelial Growth Factor as a Non-Invasive Marker of Pulmonary Vascular. Respir Res. Mar. 2007; 8: 22-29.

Sharma SB, Dwivedi S, Prabhu KM, Singh G, Kumar N, Lal MK. Coronary Risk Variables in Young Asymptomatic Smokers. Indian J Med Res. Sep. 2005; 122: 205-10.

Dietrich M, Block G, Hudes M, Morrow JD, Norkus EP, Traber MG, Cross CE, Packer L. Antioxidant Supplementation Decreases Lipid . Biomarkers & Prevention. Sep. 2002; 11: 7-13.

Chen HJ, Wu CF, Hong CL, Chang C. Urinary Excretion of 3,N4-Etheno-2'-Deoxycytidine in Humans as a Biomarker of Oxidative Stress: Chem Res Toxicol. May 2004;17:896-903.

Asami S, Manabe H, Miyake J, Tsurudome Y, Hirano T, Yamaguchi R, Itoh H, Kasai H. Cigarette Smoking Induces an Increase in Oxidative. Carcinogenesis. Jun. 1997; 18:1763-6.

Kasahara Y, Tuder RM, Cool CD, Lynch DA, Flores SC, Voelkel NF. Endothelial Cell Death and Decreased Expression. Am J Respir Crit Care Med.Jul. 2000; 163:737-44.

Conklin BS, Zhao W, Zhong D-S, Chen C. Nicotine and Cotinine Up-Regulate Vascular Endothelial Growth Factor Expression. Am J Pathol. Feb. 2002; 160: 413-418.

Vivanco I, Sawyers CL. The Phosphotidylinositol 3-Kinase /AKT Pathway in Human Cancer. Nat Rev Cancer. Jul. 2002; 2: 489-501.

Tsurutani J, Castillo SS, Brognard J, Granville CA, Zhang C, Gills JJ, Sayyah J, Dennis PA. Tobacco Components Stimulate . Carcinogenesis. Mar. 2005; 26: 1182-1195.

Kim I, Kim JH, Moon SO, Kwak HJ, Kim NG, Koh GY. Angiopoietin-2 at High Concentration Can Enhance Endothelial Cell Survival. Oncogene. Jul. 2000; 19: 4549-4552.

Kubota Y, et al. Cooperative Interaction of Angiopoietin-like Proteins 1 and 2 in Zebrafish Vascular Development. PNAS. Jul. 2005; 102: 13502-13507.

Tsuji T, Aoshiba K, Nagai A. Alveolar Cell Senescence in Patients With Pulmonary Emphysema. Am J Respir Crit Care Med. Aug. 2006; 174:886-93.

Yokohori N, Aoshiba K, Nagai A. Increased Levels of Cell Death and Proliferation in Alveolar Wall Cells in Patients With Pulmonary Emphysema. Chest. Oct. 2004; 125: 626-632.

Valdes AM, Andrew T, Gardner JP, Kimura M, Oelsner E, Cherkas LF, Aviv A, Spector TD. Obesity, Cigarette Smoking, and Telomere . Lancet. Jun. 2005; 366: 662-664.

Von Zglinicki T. Oxidative Stress Shortens Telomeres. Trends Biochem Sci. Jul. 2002; 27: 339-344.

Andersen MR, Walker LR, et al. Reduced Endothelial Nitric Oxide Synthase Activity and Concentration in Fetal Umbilical Veins . Am J Obst and Gyn.Dec. 2003; 191: 346-351.

Hoshino S, Yoshida M, et al. Cigarette Smoke Extract Induces Endothelial Cell Injury Via JNK Pathway. Biochem Biophys Res Commun. Feb. 2005; 329:58-63.

Michaud SE, Ménard C, Guy L-G, Gennaro G, Rivard A. Inhibition of Hypoxia-Induced Angiogenesis by Cigarette Smoke Exposure: . FASEB J. 2003; EPUB Apr. 2003 22.

* cited by examiner

US 7,972,795 B2

ANGIOPOIETIN-LIKE 2 AS A BIOMARKER OF VASCULAR ENDOTHELIAL CELL ABNORMAL FUNCTION AND SENESCENCE

This application claims priority from U.S. Provisional Patent Application Ser. No. 60/814,894 filed Jun. 20, 2006, which is hereby incorporated by reference in its entirety.

FIELD OF THE INVENTION

The present invention relates to the general field of medical methods and compounds and is particularly concerned with the use of angiopoietin-like 2 as a biomarker of vascular endothelial cell abnormal function and senescence.

BACKGROUND OF THE INVENTION

Tobacco smoke contains pro-oxidant substances, mutagens and carcinogens (1) and evidence linking cigarette smoke exposure with cardiovascular disease and cancer is clearly present. The primary role of cigarette smoking in coronary artery disease (CAD) is to cause injury to the vascular endothelium by direct cytotoxicity, leading to endothelial dysfunction and atherosclerosis (2). In both animal and human models, several studies have demonstrated that both active and passive cigarette smoke exposure were associated with a decrease in vasodilatory function (3-4). In addition to vasomotor dysfunction, potential pathways and mechanisms for smoking-induced cardiovascular disease are inflammation, platelet dysfunction, alteration of antithrombotic and prothrombotic factors, alteration in fibrinolysis and modification of lipid profile (5). Cessation of smoking (6-9) and antioxidant therapy (10) both improve endothelial function in smokers, suggesting a role for increased levels of oxygen-derived free radicals (11). The precise mechanism of smoking-related endothelial dysfunction is not well understood and is very likely multifactorial. In humans, the situation is even more complex since chronic smokers can cumulate various risks factors for CAD such as obesity, hypertension, dyslipidemia and diabetes, pathologies themselves exacerbated by smoking.

At the cellular level, aging of healthy vascular ECs leads to senescence, a state of permanent growth arrest (12-13). Senescence is characterized by specific changes in cell morphology and gene expression, which reduce EC function (14-15) and thus are proposed to be pro-atherogenic (16-17). Senescence can be triggered by cell divisions that lead to cumulative telomere attrition down to a threshold length at which cells enter the so-called replicative senescence (18). Cellular senescence can also occur prematurely following exposure to multiple types of stress (stress-induced senescence), independently of replicative age, such as oxidative stress (19), DNA damage and mitogenic stress (13).

The atherosclerotic lesion develops through age. It can lead to coronary artery disease (CAD), promoting cardiac ischemia and death. Cardiovascular diseases are associated with numerous risk factors such as aging, diabetes, obesity, hypertension, dyslipidemia but also viral and bacterial infection. The first target of these risk factors, all associated with a rise in oxidative stress, is the vascular endothelium. Vascular endothelial cells (ECs) become dysfunctional before clinical signs of vascular diseases. If a biomarker could predict the level of damage of the endothelium, a clinician could intervene early in the development of the pathology and prevent its outcome, reducing costs for the health system and benefits to the patient.

Hence, there exists a need for a biomarker of vascular endothelial cell abnormal function and senescence. An object of the present invention is therefore to provide a biomarker of vascular endothelial cell abnormal function and senescence.

SUMMARY OF THE INVENTION

In a broad aspect, the invention provides a method for assessing a physiological state of a mammal. The method includes:
  obtaining from the mammal a biological sample;
  measuring the expression of angiopoietin-like 2 in the biological sample; and
  assessing the physiological state of the mammal by comparing the measured expression of the angiopoietin-like 2 to a predetermined normal expression level in normal subjects, wherein an increase in angiopoietin-like 2 level over the predetermined normal expression level indicates an abnormal physiological state.

In a variant, the biological sample comprises mammalian cells, measuring the expression of angiopoietin-like 2 comprises measuring the expression of angiopoietin-like 2 in the mammalian cells; and assessing the physiological state of the mammal comprises assessing the physiological state of the mammal by comparing the measured expression of the angiopoietin-like 2 to a predetermined expression level in normal cells, wherein an increase in angiopoietin-like 2 level over the predetermined expression level indicates an abnormal physiological state.

In some embodiments of the invention, the mammalian cells comprise endothelial cells, for example any type of vascular endothelial cells or vascular endothelial arterial cells.

In some embodiments of the invention, measuring the expression of angiopoietin-like 2 in the mammalian cells comprises measuring angiopoietin-like 2 mRNA levels, for example using quantitative RT-PCR. Also, in some embodiments, assessing the physiological state of the mammal comprises assessing the physiological state of the mammal by comparing a ratio between the measured expression of the angiopoietin-like 2 and a measured expression of a reference protein to a predetermined ratio between the expression level of the angiopoietin-like 2 in normal cells and the expression of the reference protein in normal cells, wherein an increase in the ratio over the predetermined ratio indicates an abnormal physiological state.

The reference protein is a protein that is expressed at predetermined levels both in normal subjects and in subjects suffering from conditions that are to be evaluated. A non-limiting example of this protein is glyceraldehyde 3-phosphate dehydrogenase (GAPDH). Predetermined normal expression levels of angiopoietin-like 2 relatively to GAPDH are found hereinbelow in the specification.

In some embodiments of the invention, the angiopoietin-like 2 expression measured is at least about 2 times greater than the predetermined expression of angiopoietin-like 2 in normal mammalian cells. In other embodiments, the angiopoietin-like 2 expression measured is at least about 5 times greater than the predetermined expression of angiopoietin-like 2 in normal mammalian cells.

In some embodiments of the invention, assessing the physiological state of the mammal comprises detecting a cellular abnormal function in the mammalian cells. For example the mammalian cells comprise vascular endothelial cells and assessing the physiological state of the mammal comprises detecting a cellular abnormal function in the vascular endothelial cells.

In other embodiments, assessing the physiological state of the mammal comprises detecting oxidative stress in the mammalian cells.

In yet other embodiments, assessing the physiological state of the mammal comprises assessing a risk of abnormal cell proliferation of the mammalian cells.

In yet other embodiments, assessing the physiological state of the mammal comprises detecting markers of chronic inflammation in the mammal.

In yet other embodiments, assessing the physiological state of the mammal comprises detecting markers of atherosclerotic lesions in the mammal.

In yet other embodiments, assessing the physiological state of the mammal comprises assessing the risk of development of atherosclerotic lesions in the mammal.

In some embodiments of the invention, the mammal is a human.

In a variant, the biological sample comprises blood; measuring the expression of angiopoietin-like 2 comprises measuring the quantity of angiopoietin-like 2 proteins in the blood; and assessing the physiological state of the mammal comprises assessing the physiological state of the mammal by comparing the measured quantity of the angiopoietin-like 2 proteins to a predetermined quantity in normal subjects, wherein an increase in angiopoietin-like 2 proteins level over the predetermined quantity indicates an abnormal physiological state.

Angiopoietin-like 2 (ANGPTL2) was identified as a potential biomarker of vascular endothelial cell (EC) abnormal function from patients with vascular disease. Its expression increases with senescence of EC. In addition, in a subgroup of patients that are active smokers, ANGPTL2 gene expression is four times greater than in non-smokers. These data suggest that ANGPTL2 is a marker of vascular EC abnormal function and can be used as an important biomarker. In addition, we propose that ANGPTL2 is likely to be a therapeutic target in all diseases associated with abnormal endothelial function associated with pathological angiogenesis in oncology, inflammatory diseases and diabetes, as well as in abnormal endothelial function associated with risk factor for cardiovascular diseases (CVD).

More specifically, EC were isolated and cultured from patients undergoing cardiac surgery (smokers, n=26; ex-smokers, n=40, non-smokers, n=20). Smokers were 11 years younger than non-smokers (p<0.05). Oxidative stress was measured by levels of 4-hydroxynonenal (HNE) by immunostaining. Gene expression was measured initially in culture by quantitative PCR (QPCR) and proteins were quantified by Western blot. Senescence was induced by serial passage and quantified by β-galactosidase staining; telomere length (RFL) was measured by Southern blot.

Expression of HNE (8.3±2.1 vs 4.5±0.5, p=0.043) and caveolin-1 (mRNA: 4.19±1.84 vs 0.41±0.08, p=0.042) were higher in smokers suggesting a greater oxidative stress. EC from smokers exhibited markers of inflammation (Angiopoietin-like 2 mRNA: 5.1±1.9 vs 0.9±0.4, p=0.034), hypoxia (VEGF-A mRNA: 7.3±1.1 vs 2.6±0.5, p=0.001) and cell damage (p53 mRNA: 0.19±0.05 vs 0.07±0.01, p=0.005). Akt activity was increased in smokers (1.4±0.3 vs 0.5±0.1, p=0.0450). EC from smokers, however, reached senescence in culture later (time to reach 50% of senescent cells: 104±5 vs 87±4 days, p=0.031) and their proliferative potential was increased (population doubling: 15±1 vs 11±1, p=0.047). RFL shortening rate (−4.7±3.9 vs −15.7±2.8 bp/day, p=0.032) and ATM (mRNA: 0.696±0.097 vs 1.271±0.399, p=0.0262) were lower in smokers suggesting a minor influence of telomeres in senescence. High oxidative stress in EC from smokers predisposes to telomere-independent senescence, which is detectable through the use of angiopoietin-like 2 as a biomarker. It is expected that the use of angiopoietin-like 2 as a biomarker is also applicable in other situations where oxidative stress occurs in ECs.

Other objects, advantages and features of the present invention will become more apparent upon reading of the following non-restrictive description of preferred embodiments thereof, given by way of example only with reference to the accompanying drawings.

DETAILED DESCRIPTION

Figure 1:
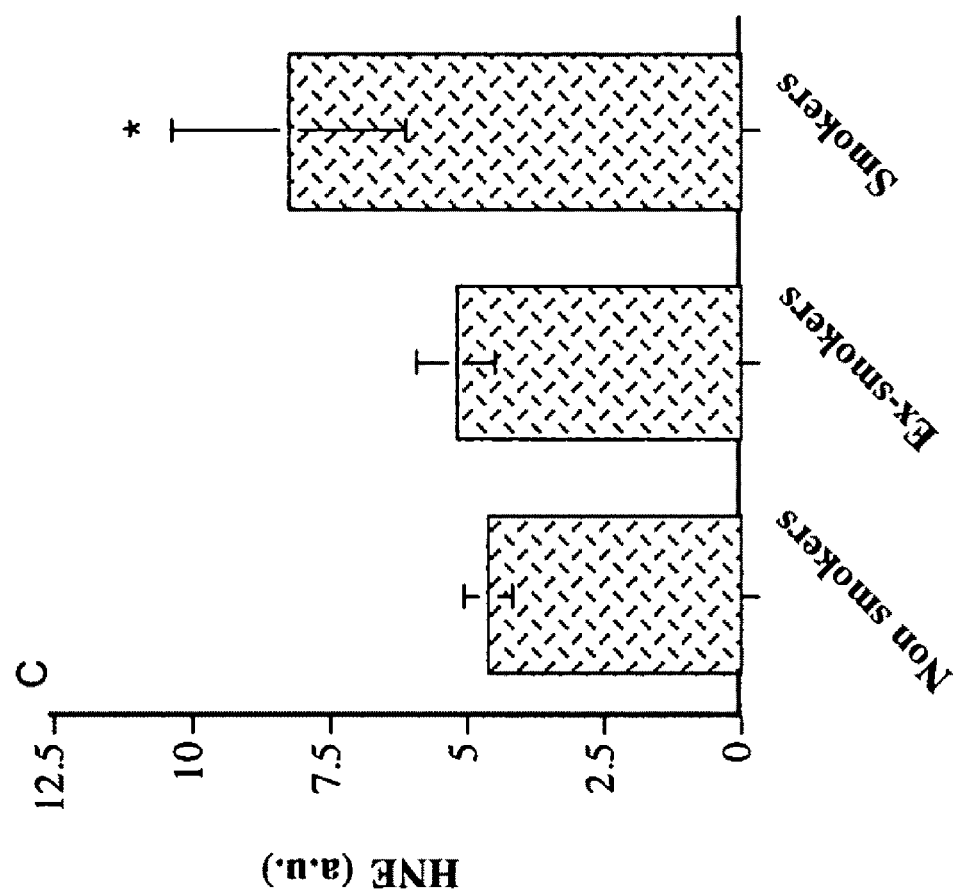
FIG. 1 illustrates the increase in lipid peroxidation in EC isolated from smokers. Total levels of 4-hydroxy-nonenal (HNE), a marker of lipid peroxidation, were estimated by immunofluorescence staining at passage 2, early in culture. DNA counterstaining was performed with TOPRO-3. The figure presents average values of total HNE in EC, corrected by the number of cells observed per slide, from non-smokers (n=8), former smokers (n=9) and smokers (n=5). Data are expressed as mean±SEM. *: p<0.05 compared to non-smokers (ANOVA with Fisher's post hoc test).

The present description refers to many public documents, the contents of which are hereby incorporated by reference in their entirety.

An objective of the present study was therefore to identify an EC senescence pathway that would explain premature CAD in chronic smokers. We found that chronic smokers with severe CAD were 11 years younger than non-smokers patients with atherosclerosis, and that EC isolated from smokers displayed unique markers of oxidative stress and cell damage. This committed endothelial cells to oxidative stress-dependent and telomere-independent senescence. It was observed that an increase in angiopoietin-like 2 is indicative of abnormal physiological state.

EXAMPLE

Methods

Clinical profile of the donors. Segments of human distal (close to the bifurcation) internal mammary arteries (n=86, Table 1), harvested with low electrocautery energy and excised with cold scissors, discarded during coronary artery bypass surgery, were used. Collection of the samples was blind. The study was approved by our institutional ethical committee and the patients gave informed consent.

Using the clinical file of the patients, the donors were divided into active smokers (n=26), former smokers (n=40) and never smokers (n=20). The information on cigarettes consumption (pack/year) of the smokers was not available; however, among the patients, 27% (7/26) had chronic obstructive pulmonary disease (COPD). The group of former smokers was heterogeneous since the duration of smoking cessation ranged from 0.1 to 30 years (average of 13.5±1.9 years). Because the cardiovascular effects of smoking are not necessarily reversible, we did not further divide this group in recent or long former smokers. Although most of smoking-induced changes are reversible after quitting, some inflammatory markers such as CRP are still higher 20 years after cessation in former smokers (8-9). Among the former smokers, 22.5% (9/40) suffered from COPD, and this was not related to the duration of smoking cessation (p>0.05). Only one patient who never smoked had COPD.

Culture of EC. Endothelial cells were isolated and cultured by an explant technique (20, 21). Cells were collected for senescence-associated β-galactosidase staining (SA-X-Gal), for reactive oxygen species (ROS) measurement, for DNA (Southern), RNA (real-time RT-PCR) and protein (Western blotting); some cells were plated on coverslips for immunostaining. Before replating, cells were counted using a hemocytometer and the population doubling level (PDL) was calculated.

More specifically, human arterial samples were cut into segments and placed on Matrigel, the endothelium facing the coating. This represented the reference day-1 of the experiment. Segments were incubated in Dulbecco's modified Eagle medium (DMEM) supplemented with 10% FBS, 10% CS, 1% penicillin-streptomycin, 90 µg/ml sodium heparin salt (Sigma), 60 µg/ml EC growth supplement (Beckton Dickinson), and 100 U/ml fungizone (Gibco), at 37° C. in a 95% air/5% $CO_2$ incubator. After approximately 1 month, cells were passaged with Dispase (Beckton Dickinson) and redistributed onto positively charged (Cell+; Sarstetd) 60 mm tissue culture plates. Cells were then maintained in culture and passaged with 0.05% trypsin-EDTA in a 1:4 ratio until replicative senescence was reached (growth arrest despite normal feeding). Cells were collected for senescence-associated β-galactosidase staining (SA-X-Gal), for reactive oxygen species (ROS) measurement, for DNA (Southern), RNA (real-time RT-PCR) and protein (Western blotting); some cells were plated on coverslips for immunostaining. Before replating, cells were counted using a hemocytometer and the population doubling level (PDL) was calculated.

β-galactosidase staining. Senescence-associated β-galactosidase (SA-X-Gal) was used as a marker of senescence (22), at each passage (from passage 2 to the latest possible passage [3-20]). The percentage of blue SA-X-Gal positive cells was determined by counting, in 4 different fields, at least 200 cells (inverted microscope Nikon TMS).

Immunofluorescence. Immunostaining was used to assess the expression and sub-cellular localization of 4-hydroxy-nonenal (HNE) (rabbit polyclonal anti-HNE, 1:200, Alpha Diagnostics). DNA counterstaining was performed by incubating EC with TOPRO-3 (2 µM; Molecular Probe). Negative controls were performed by omitting the primary antibodies during the protocol. Cells were visualized using a confocal microscope. Semi-quantitative analysis was performed by measuring the average total fluorescence intensity (HNE) from 4-5 different pictures from the same coverslip. Values are expressed in arbitrary units (a.u.) of fluorescence (FIG. 1).

Figure 2:
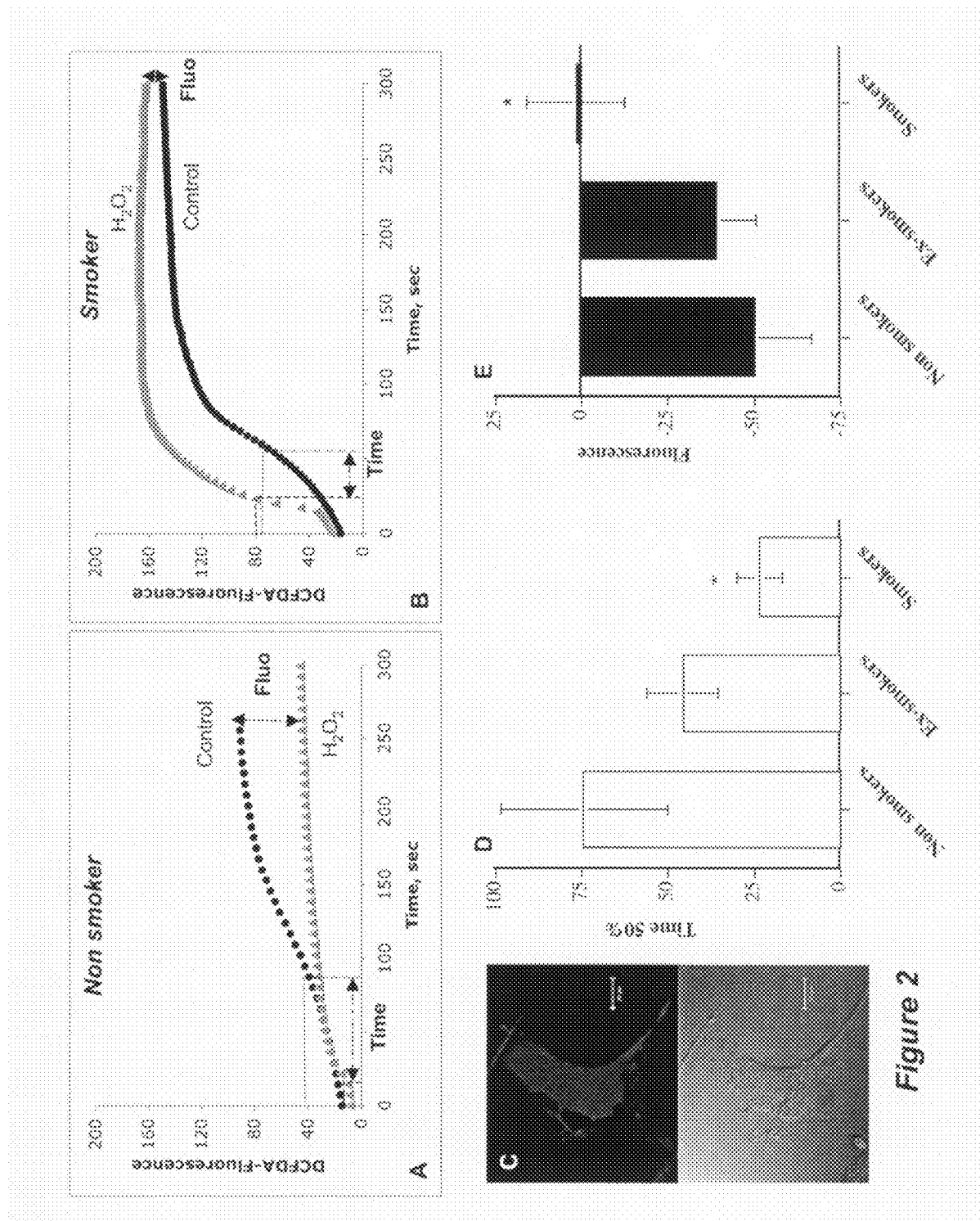
FIG. 2 illustrates the measurement of reactive oxygen species (ROS) in live EC. Reactive oxygen species (ROS) were measured in live cells using the non-specific fluorescent dye CM-$H_2$DCFDA, at passage 2, early in culture. Cells were loaded with 5 µM dye for 30 min, and the fluorescent signal recorded at 488 nm with a confocal microscope, using specific parameters for the laser light (see methods for details) (C). EC were stimulated with the laser light until the fluorescent signal saturated, at a scan speed of 2.56 µsec/pixel. Then, cells in a different field were stimulated with the laser light in presence of 100 µM of $H_2O_2$, in order to get maximal oxidative activity, and the signal was recorded until saturation. From the 2 saturation profiles, the time needed to reach 50% of saturation in both control and $H_2O_2$ stimulated cells was measured. The maximal fluorescence intensity in both control and $H_2O_2$ stimulated cells was recorded. Δtime 50%$_{(control-H2O2)}$ and Δfluorescence max$_{(H2O2-control)}$ were calculated: the shorter Δtime and/or the smaller Δfluorescence, the faster the oxidation process within the cells. This method estimates the antioxidant capacities of the cells and indirectly provides the ROS levels. Example of saturation profile in EC from a non-smoker (A) and a smoker (B) patient. Average Δtime 50%$_{(control-H2O2)}$ (D) and Δfluorescence (E) in EC from non-smokers (n=6), former smokers (n=9) and smokers (n=4). Data are expressed as mean±SEM. *: p<0.05 compared to non-smokers (ANOVA with Fisher's post hoc test).

Reactive oxygen species quantification. Reactive oxygen species (ROS) levels were measured in live cells. 5-(and -6)-chloromethyl-2',7'-dichlorodihydrofluorescein diacetate acetyl ester (CM-$H_2$DCFDA, Molecular Probes) was used as a non-specific marker of ROS. Cells were loaded with 5 µM of CM-DCFDA (in physiological salt solution) for 30 min at 37° C., washed and let recover for 10-15 min at 37° C. The fluorescence was then observed at 488 nm under a microscope (LSM 510 Zeiss microscope). Negative control consisted in unstained cells (autofluorescence). hIMA EC used in this study displayed an unstable basal level of fluorescence which significantly increased over time. In order to bypass this problem, which is not observed using healthy cells (data not shown), we modified the protocol that usually only consists in measuring the intensity of ROS-fluorescence: hIMA EC were exposed to the laser light until the fluorescent signal saturated. Then, cells were exposed to 100 µM $H_2O_2$ in order to get maximal oxidative activity, and the fluorescent signal was recorded until saturation, in a different field (FIG. 2). Identical parameters were used for all experiments (objective 63×1.4 plan-Apochromat oil, laser Argon 488 nm, 0.1% transmission; dichroic mirror HFT 488 with filter LP505, pinhole size 1.7 Airy unit). The frame size of the images was 512×300 pixels and the scan speed was 2.56 μsec/pixel. From the two saturation profiles analyzed with LSM 510 software, the time needed to reach 50% of saturation in both control and $H_2O_2$ stimulated cells was measured. The maximal fluorescence intensity in both control and $H_2O_2$ stimulated cells was recorded. We calculated $\Delta$time 50%$_{(control-H2O2)}$ and $\Delta$fluorescence max$_{(H2O2-control)}$: the shorter $\Delta$time and/or the smaller $\Delta$fluorescence, the faster the oxidation process within the cells. This method reflects the antioxidant capacities of the cells and indirectly provides the ROS levels.

Telomere length measurement. Cells were grown in 75 cm$^2$ flasks at early and subsequent passages until replicative senescence was reached. DNA extraction was performed with a phenol/chloroform/isoamyl alcohol technique, precipitated using ethanol 95% and dissolved in Tris-HCl (10 mM, pH 8.6). Restriction fragments length (RFL) were quantified using a Southern blot technique (23).

Western blotting. Nuclear and cytosolic proteins were extracted separately using a nuclear and cytoplasmic extraction kit (Pierce Biotechnology) in the presence of 10× protease inhibitor cocktail (Pierce Biotech). 25 μg of proteins were separated on a SDS-polyacrylamide gel (ProteanIIXi system). The primary antibodies were either mouse anti-p53 (1:200, Upstate), anti-Akt/phospho Akt (1:1000, Cell Signaling), goat anti-AngioPL2 (1:200, Sigma) or mouse anti-GAPDH (1:100,000, Ambion). Nuclear protein expression of p53 and cytosolic expression of Phospho-Akt and ANGPTL2 were reported as the ratio protein/GAPDH and expressed as arbitrary units.

Real-time RT-PCR. Total RNA was isolated using RNeasy kit (Qiagen) and reverse-transcribed into first-strand complementary DNA by MMLV using random hexamer primers. Real-time polymerase chain reaction (PCR) was carried out on diluted RT products using the DNA-binding dye SYBR Green I for the detection of PCR products (Mx3005P system, Stratagene) according to the manufacturer's instruction. Serial dilutions (100 ng to 1 pg) of human aortic EC (hAoEC, Cambrex) total RNA were used as standard. The following primers designed by primer express (Version 2.0) were used in order to quantify gene expression of Cox-2, AngioPL-2, h-HIF-1, VEGF-A, p53, p21, p16, caveolin-1, ATM and GAPDH:

| Primers | Forward (5'-3') | Reverse (5'-3') |
|---|---|---|
| Cox-2 | TGGCGCTCAGCCATACAG | GGTACAATCGCACTTATACTGGTCAA |
|  | (SEQ ID NO: 1) | (SEQ ID NO: 2) |
| h-HIF-1 | CATCATCACCATATAGAGATACTCAA | TCTGAGCATTCTGCAAAGCTAGT |
|  | (SEQ ID NO: 3) | (SEQ ID NO: 4) |
| p53 | TGAGGTTGGCTCTGACTGTA | TTCTCTTCCTCTGTGCGCCG |
|  | (SEQ ID NO: 5) | (SEQ ID NO: 6) |
| p21 | GGACCTGTCACTGTCTTGTA | TGTAGGACCTTCGGTGACTG |
|  | (SEQ ID NO: 7) | (SEQ ID NO: 8) |
| p16 | CATAGATGCCGCGGAAGGT | TGTAGGACCTTCGGTGACTG |
|  | (SEQ ID NO: 9) | (SEQ ID NO: 10) |
| AngioPL2 | GCAATGCGGGTGACTCCTT | TACCAGGACGGAGTCTA |
|  | (SEQ ID NO: 11) | (SEQ ID NO: 12) |
| VEGF-A | GAGGGCAGAATCATCACGAA | AGGAGTCCAACATCACCATG |
|  | (SEQ ID NO: 13) | (SEQ ID NO: 14) |
| Caveolin-1 | GCTGAGCGAGAAGCAAGTGT | TGGTGAAGCTGGCCTTCCAA |
|  | (SEQ ID NO: 15) | (SEQ ID NO: 16) |
| ATM | GGCAGCTGATATTCGGAGGA | CATCTTGGTCACGACGATAC |
|  | (SEQ ID NO: 17) | (SEQ ID NO: 18) |
| GAPDH | TGAAGGTCGGAGTCAACGGA | CATTGATGACAAGCTTCCCG |
|  | (SEQ ID NO: 19) | (SEQ ID NO: 20) |

The mRNA level in each sample was calculated relative to GAPDH. PCR was performed at 95° C. for 10 minutes, and then for 40 cycles at 95° C. for 30 seconds and 55° C. for 1 minute and 72° C. for 30 seconds. A final dissociation cycle was done at 95° C. for 1 minute, 55° C. for 30 seconds and 95° C. for 30 seconds.

Statistical analysis of the data. Continuous data are presented as mean±sem, with n indicating the number of patients. Appropriate univariate analysis (t-test or ANOVA with fisher's post hoc test) was used. A $p<0.05$ was considered statistically significant.

Results

Patient characteristics. In this study, we used discarded samples of the distal internal mammary artery from patients undergoing coronary artery bypass graftsurgery. The clinical parameters of the patients were evenly distributed between smokers and non-smokers, except for the age of the donor: smokers were 11 years younger when compared to non- and former smokers ($p<0.05$) (Table 1).

Initial markers in EC:

Early in culture (passage 2, $\Sigma PDL=4.5\pm1.4$, % of X-Gal positive cells=$5.1\pm0.8$, n=59), several initial markers of EC were evaluated: oxidative stress, telomere length and gene expression.

HNE: Initial levels of HNE, a marker of lipid peroxidation, were significantly higher in EC from smokers compared to non-smokers ($8.3\pm2.2$ versus $4.7\pm0.4$ arbitrary units of fluorescence, p=0.0302) (FIG. 1). Initial levels of HNE were not significantly (inversely) correlated with the time duration of smoking cessation (r=−0.342, p=0.1517, n=18; data not shown).

ROS: We used a new approach to estimate the endogenous initial level of ROS (FIG. 2): the antioxidant capacities of live cells challenged to a pro-oxidant stimulus (laser light with or without exogenous $H_2O_2$ 100 µM) were quantified. The antioxidant capacity of live cells challenged to a pro-oxidant stimulus indirectly reflects endogenous ROS levels: the lower the antioxidant capacities, the higher the ROS levels. FIG. 2 illustrates the significantly lower antioxidant capacities in smokers compared to non-smokers: in EC from smokers, the ROS-fluorescent signal was similar (small $\Delta time_{50\%}$ and $\Delta Fluorescence_{max}$) when cells were stimulated with either laser light or $H_2O_2$ solution. In contrast, EC from non-smokers exhibited a slow and weak signal to the laser light and to $H_2O_2$, respectively, reflecting strong antioxidant defenses.

RFL i: Initial telomere length was similar between groups (FIG. 3A) ($8.9\pm0.4$; $9.3\pm0.3$; $9.0\pm0.2$ kbp; in non-smokers, former smokers and active smokers, respectively).

Initial genes expression: Angiopoietin-like protein 2 (ANGPTL2) could, as angioPL3 (24), play a role in endothelial dysfunction and inflammation (25). Initial ANGPTL2 gene levels were four times higher (p=0.0406) in EC from smokers compared to non-smokers or former smokers (Table 2). Similarly, initial gene levels of the angiogenic factor VEGF-A were 3 times higher (p=0.0005) in EC from smokers compared to non-smokers or former smokers (Table 2). The initial gene expression of the tumor suppressor gene p53 was 2 fold higher (p=0.0087) in EC from smokers (Table 2). Overexpression of caveolin-1, an antiproliferative protein, is known to promote oxidative stress-induced senescence (26). The initial gene expression of caveolin-1 was 8 fold higher (p=0.0416) in EC from smokers (Table 2). Caveolin-1 expression positively correlated with the oxidative stress marker HNE (p=0.0009, $r^2=0.722$, n=10; data not shown) and with the inflammatory marker Cox-2 (p=0.0366, $r^2=0.401$, n=10; data not shown). On the other hand, initial ATM expression, a protein known to function as transducer of telomere dysfunction (27, 28), was two-fold lower in EC from smokers (p=0.0262) (Table 2). Expression of hypoxia-induced-factor-1 (HIF-1), Cox-2, p21 and p16 were not significantly different between groups (Table 2).

Figure 4:
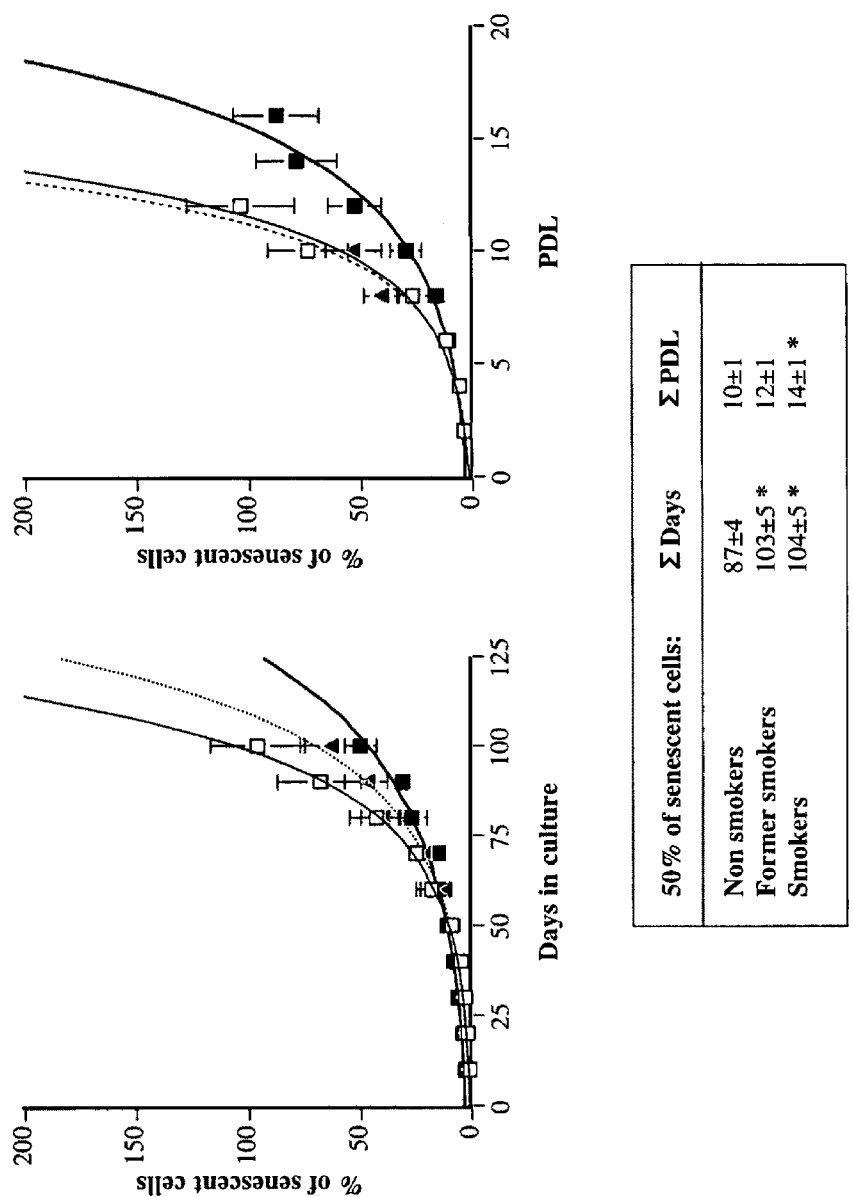
FIG. 4 illustrates the delayed apparition of passage-induced senescence in EC from smokers. Profile of senescence, quantified by senescence associated β-galactosidase at pH 6 and induced by serial passage in culture, in EC isolated from non-smokers, empty squares, (n=16), former smokers, triangles, (n=34) and smokers, black squares (n=25) added text. Data are expressed as mean±SEM. *: p<0.05 compared to non-smokers (ANOVA with Fisher's post hoc test). From the profiles of senescence, the time (ΣDays) and the number of cell divisions (ΣPDL) reached when 50% of the cells are senescent, were calculated. Derived from these parameters, it appears that EC from smokers reach cellular senescence later and proliferate more than EC isolated from non-smokers.

Senescence profile: Cellular senescence was induced by serial passages. Despite markers of oxidative stress and cell damage, senescence appeared later in EC from smokers compared to non-smokers (FIG. 4): the time needed to reach 50% of senescence was longer by 18 days in smokers (p=0.0313). PDL reached at 50% of senescence was higher in smokers (p=0.0295) (FIG. 4), suggesting higher replicative potential.

Telomere attrition: In EC from smokers, despite the fact that cells eventually reached senescence, telomere shortening rate was significantly (p=0.0093) reduced when compared to non-smokers (FIG. 3B), suggesting a minor role of telomere shortening in senescence of cells from smokers. Furthermore, initial RFL measured in EC from smokers do not correlate with the propensity to develop senescence (p=0.468), while in non-(p=0.0361) and former smokers (p=0.0042, data not shown), short initial RFL predicts the development of early senescence later in culture (FIGS. 3C and D).

Figure 5:
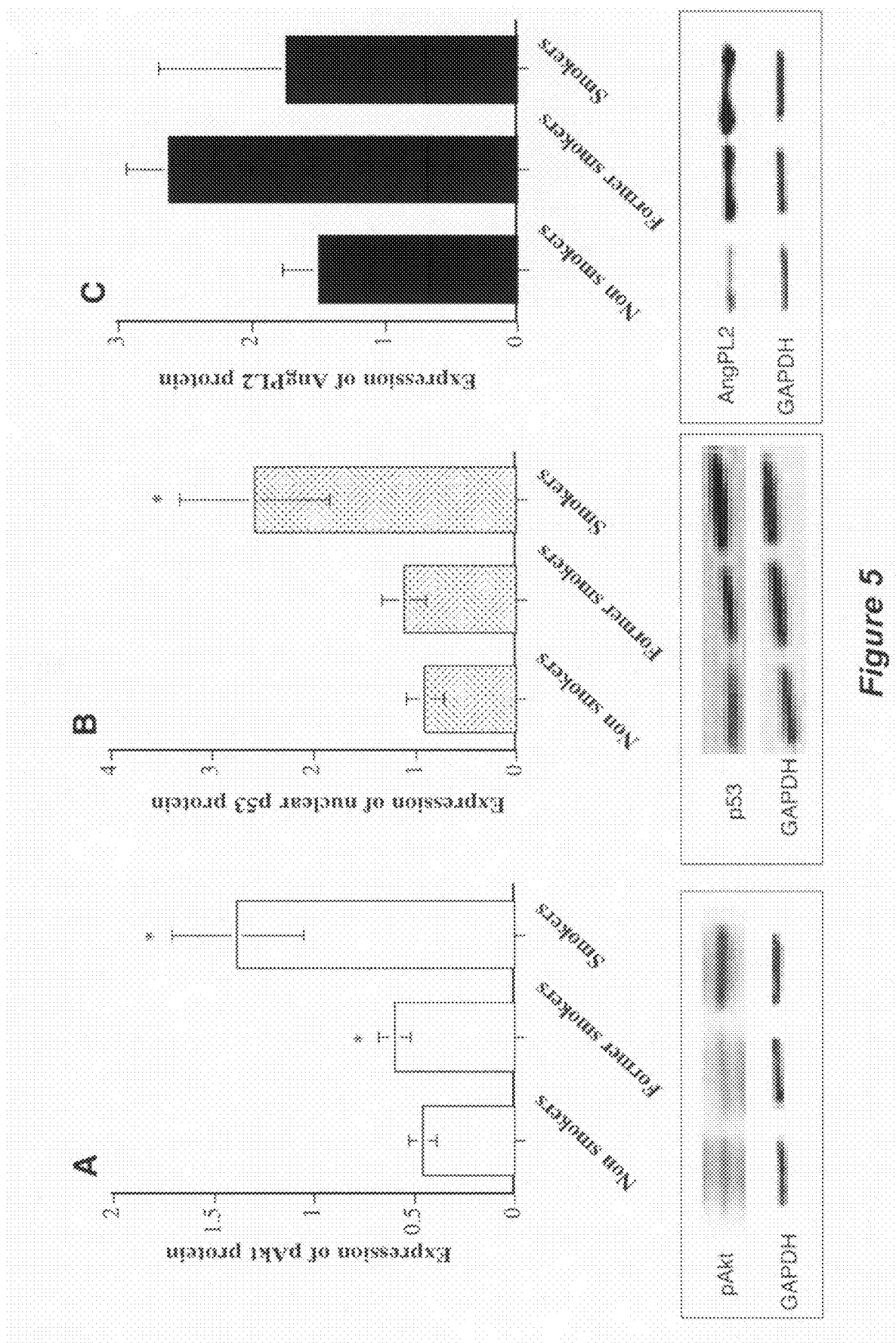
FIG. 5 illustrates the phospho-Akt, p53 and angiopoietin-like 2 protein expression in EC from smokers. Protein expression was measured by Western blot, and normalised by GAPDH expression. (A) Phospho-Akt expression, corrected by total Akt expression, was measured in EC isolated from non-smokers (n=6), former smokers (n=12) and smokers (n=16). (B) Nuclear p53 protein expression was measured in EC isolated from non-smokers (n=11), former smokers (n=11) and smokers (n=10). (C) Cytosolic ANGPTL2 expression was measured in EC isolated from non-smokers (n=7), former smokers (n=9) and smokers (n=4). Representative gels are shown below. Data are expressed as mean±SEM. *: p<0.05 compared to non-smokers (ANOVA with Fisher's post hoc test).

Impact of smoking on protein expression of pAkt, p53 and ANGPTL2: FIG. 5 illustrates that in hIMA EC isolated from smokers, pAkt expression, a marker of cell survival and endothelial dysfunction (29, 30) is increased when compared to non-smokers (p=0.0450) and former smokers (p=0.0334). Similarly, expression of the tumor suppressor p53 is higher in smokers (p=0.0378) (FIG. 5). No significant differences in ANGPTL2 protein expression were observed among the different groups (FIG. 5). It is believed that this is caused by a relatively rapid excretion of the ANGPTL2 in the blood after it has been synthesized. It is therefore hypothesized that measuring protein levels of ANGPTL2 in blood could provide another method of assessing a physiological state of a mammal.

Simple linear regression between ANGPTL2 and EC markers: In order to determine if initial levels of ANGPTL2 mRNA could predict abnormal cell proliferation and senescence (31) in smokers, simple linear regression were made between this parameter and EC markers (Table 3). High initial levels of ANGPTL2 mRNA were found to be associated with late senescence (p=0.041), high replicative potential (p=0.0001), low telomere shortening rate (p=0.0136), high initial levels of VEGF-A (p=0.009), p53 (p=0.0039) and HIF-1 (p=0.0215). This suggests that EC exposed to chronic hypoxia in smoking patients up-regulate the expression of angiogenic factor such as VEGF and ANGPTL2, and this will influence the culture-induced senescence.

COPD as a an independent marker of abnormal EC function

Current understanding of the pathobiology of COPD suggests different biomarkers as potential candidates, such as increased oxidative stress (32) and VEGF (33). In EC isolated from smoker and ex-smoker patients with COPD, we found that gene expression of ANGPTL2, VEGF-A, p21 and p53 were significantly elevated (Table 4). In contrast, initial gene expression of HIF-1, p16, caveolin-1, ATM and Cox-2 were not affected in EC from patients with COPD, and HNE or Akt activity were not altered (Table 4).

Discussion

We found that EC isolated from smokers display various markers of oxidative stress and cell damage, and that culture-induced senescence was mediated through telomere-independent pathways. In addition, our data suggest that ANGPTL2 could play a determinant role in the ROS-induced abnormal cellular senescence in smokers.

Initial EC markers (oxidative stress, gene expression of various signaling molecules, Table 2) show that EC isolated from smokers are dramatically different from non-smokers. These initials parameters reflect the in vivo situation after years to decades of chronic exposure to thousands of toxic, carcinogenic and mitogenic molecules of tobacco. Cigarette smoke contains also large quantities of free radicals and pro-oxidant molecules (11). Accordingly, we report high initials levels of HNE, a marker of lipid peroxidation, and low anti-oxidant capacities in EC isolated from smokers, compared to non-smokers (FIGS. 1 and 2). Former smokers represent an intermediate group. Furthermore, we found that caveolin-1 gene expression was increased in EC from smokers and positively correlated with HNE levels. The fact that smoking is associated with increased oxidative stress has been previously reported: in serum and plasma from smokers, high levels of malondialdehydes (34) and $F_2$-isopostane (35) were observed. Oxidative-DNA damage products were measured in urinary samples (36) and lung tissues (37) from smokers. Altogether, these data confirm that chronic exposure to tobacco induces potent chronic oxidative stress that could lead to EC damage. We also observed higher initial VEGF-A gene expression in EC from smokers, which could be the result of chronic hypoxia. Hypoxia is a strong inducer of both VEGF and VEGF receptor genes, and VEGF is a trophic factor required for EC survival (38). These abnormal initial levels of VEGF could explain the high replicative potential of EC from smokers in culture. In contrast, we did not observe an abnormal initial gene expression of the hypoxia-induced factor HIF-1, but high levels of ANGPTL2 positively correlated with high levels of HIF-1 as well as with high levels of VEGF-A (Table 3). Increased mRNA and protein levels of VEGF were previously reported in pig carotid arteries acutely exposed to nicotine (39). In addition to oxidative stress and hypoxia markers, EC from smokers displayed markers of chronic inflammation, early in culture: an increase in gene expression of ANGPTL2 was measured in EC from smokers, especially in patients with COPD, a pathology characterized by a chronic inflammation of the lungs.

ANGPTL2 is a novel growth factor, and its function has not yet been elucidated. It could be involved in the abnormal vasculature of the diabetic and in endothelial inflammation (25). ANGPTL2 has also been reported to promote angiogenesis by activating the Pl3K/Akt pathway (31). This is in accordance with our data, since we observed that ANGPTL2 gene expression was associated with increased VEGF-A gene expression and high replicative potential (Table 3). We also observed increased pAkt protein expression in EC from smokers (FIG. 5), which could, in concert with VEGF and ANGPTL2, promote cell growth and cell survival, in response to chronic stress associated with smoking. The phosphatidylinositol 3-kinase (Pl3K)/Akt is likely to be an important pathway in tobacco related cancer because it contributes to tumorigenesis and tumor growth by promoting cell survival (40, 41). In EC, Akt pathway also mediates anti-apoptotic effects via Angiopoietins-Tie2 systems (42). Kubota et al. reported that similar to angiopoietin 2, ANGPTL2 displays anti-apoptotic activity in endothelial cells through Pl3K/Akt (43).

It has also been reported that Akt activity increases with cellular senescence (29). This senescence could lead to vascular dysfunction and inflammation (29). In accordance with this concept, we observed that EC isolated from smokers which displayed higher ROS, higher pAkt, and higher ANGPTL2, also expressed both higher gene and protein p53 levels. p53 plays important role in multiple cellular functions including senescence (13). Cellular senescence has been described to be mediated by two major pathways: senescence can be triggered by cell divisions which leads to cumulative telomere attrition down to a threshold length at which cells enter the so-called replicative senescence (18). Cellular senescence can also occur prematurely following exposure to multiple types of stress (stress-induced senescence), independently of replicative age (19) through p53-p21 pathway (13).

Figure 3:
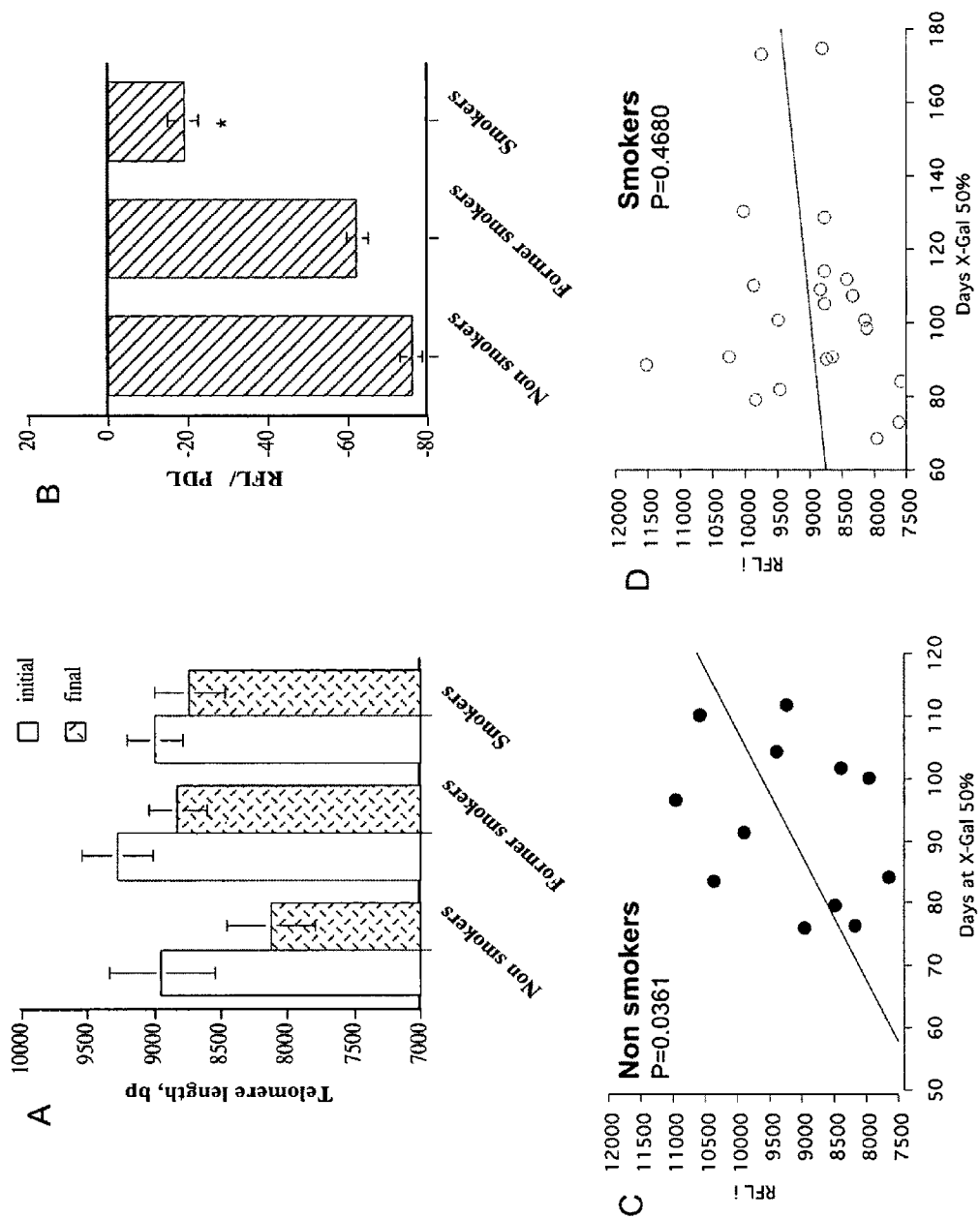
FIG. 3 illustrates the low telomere shortening in EC from smokers. Telomere length (RFL) was measured by Southern blot initially (passage 2) and when cells reached senescence (A). Telomere shortening was then calculated (ΔRFL) and corrected by the number of cell divisions performed (ΣPDL) in EC from non-smokers (n=16), former smokers (n=30) and smokers (n=21). Data are expressed as mean±SEM. *: p<0.05 compared to non-smokers (ANOVA with Fisher's post hoc test) (B). Simple linear regression between the marker of propensity to develop senesence (Time to reach 50% of senescent EC, days) and initial telomere length (bp), in EC from non-smokers (C) (r=0.526, n=15, p=0.0361) and in EC from smokers (D) (r=0.164, n=21, p=0.4680).

Higher cell turnover, leading to premature senescence, has been previously described in lung tissues from smokers with emphysema when compared to smokers or non-smokers (with lung cancer) (44-45). We observed an increase in the replicative potential, associated with upregulation of VEGF and pAkt, despite an increase in gene and protein tumor suppressor p53 expression. Since cell death was not quantified in our study, we do not know if the increase in replication potential corresponds to an increase in cell turnover. But, since cell senescence was in fact delayed by 18 days in EC from smokers compared to non-smokers (FIG. 4), we believe that cell turnover was not accelerated in these cells. Endothelial cells eventually aged, and senescence was established. The pathway of senescence differs in EC from smokers and non-smokers. In smokers, the replicative senescence seems minimal since telomere shortening was small. Furthermore, telomere length was not correlated with the propensity to develop senescence (FIG. 3). Finally, ATM gene expression was lower in EC from smokers (Table 2), suggesting lower telomere instability. On the other hand, the massive oxidative stress in EC isolated from smokers drives the stress-induced senescence pathway, as suggested by the upregulation of caveolin-1 gene expression in EC from smokers (Table 2). This contrasts with the work of Valdes (46) where telomere shortening, measured in white blood cells, was greater in smoking women. Our results also contradict the theory of Von Zglynicki (47), where high oxidative stress enhances telomere shortening in fibroblasts. Two possibilities could explain these discrepancies: a higher telomerase activity in smokers or implication of the ALT pathway. We observed no difference in nuclear and cytosolic h-TERT activity between EC from smokers or non-smokers (data not shown), suggesting that telomere shortening was not compensated in EC from smokers by a higher telomerase activity.

In summary, we report that EC from chronic smokers are predisposed to stress-induced senescence but not to telomere-dependent pathways.

We believe that our study provides new insight in the field of smoking and cellular senescence because we used EC isolated directly from smoker patients, i.e., our study uses cells that have been exposed chronically for years to decades to the toxicity associated with smoking. Similar to our approach, some work has been published using HUVEC from smoking mothers (48), but exposure of EC to tobacco in this case is limited to 9 months. An alternative is to incubate healthy cells to the serum isolated from smokers (3, 11), but the most commonly used approach is to expose healthy cells or animals to cigarette smoke extract or cigarette smoke condensate (1, 49, 50). The main disadvantage, however, is that only acute effects of smoking can be reproduced.

In conclusion, our data suggest that EC from smokers display evidences of long-term exposure to oxidative stress, hypoxia and inflammation. This predisposes to abnormal cell proliferation in culture and development of cellular senescence. The pathway mediating senescence appears to be telomere-independent and mainly driven by oxidative stress. ANGPTL2 could be a novel mediator in the turnover of endothelial cells exposed chronically to tobacco-related substances. Whether ANGPTL2 is such a mediator or not, increased expression of the ANGPTL2 gene in ECs is indicative of oxidative stress and also abnormal cell function, abnormal cell proliferation, and chronic inflammation. This pathway could participate in the development of premature CAD in chronic smokers.

While the experiments described herein concerned oxidative stress in human endothelial cells, one of ordinary skilled in the art will readily appreciate that these experiments may be predictive of biological effects in humans or other mammals and/or may serve as models for use of the present invention in humans or other mammals for indicating oxidative stress in any other suitable tissue.

Although the present invention has been described hereinabove by way of preferred embodiments thereof, it can be modified, without departing from the spirit and nature of the subject invention as defined in the appended claim.

REFERENCES

1. Narayan S, Jaiswal A S, Kang D, Srivastava P, Das G M, Gairola C G. Cigarette smoke condensate-induced transformation of normal human breast epithelial cells in vitro. Oncogene. 2004; 23: 5880-9.
2. Blann A D, Mc Collum C N. Adverse influence of cigarette smoking on the endothelium. Thromb Haemost. 1993; 70: 707-711.
3. Barua R S, Ambrose J A, Eales-Reynolds L J, De Voe M C, Zervas J G, Saha D C. Heavy and light cigarette smokers have similar dysfunction of endothelial vasoregulatory activity. An in vivo and in vitro correlation. J Am Coll Cardiol. 2002; 39: 1758-1763.
4. Celemajer D S, Adams M R, Clarkson P et al., Passive smoking and impaired endothelium-dependent arterial dilatation in healthy young adults. N Engl J Med. 1996; 334: 150-154.
5. Ambrose J A, Barua R S. The pathophysiology of cigarette smoking and cardiovascular disease. An update. J Am Coll Cardiol. 2004; 43: 1731-1737.
6. Kondo T, Hayashi M, takeshita K, Numaguchi Y, Kobayashi K, Iino S, Inden Y, Murohara T. Smoking cessation rapidly increases circulating progenitor cells in peripheral blood in chronic smokers. Arterioscler Thromb Vasc Biol. 2004; 24: 1442-1447.
7. Moreno H Jr, Chalon S, Urae A, Tangphao O, Abiose A K, Hoffman B B, Blaschke T F. Endothelial dysfunction in human hand veins is rapidly reversible after smoking cessation. Am J Physiol. 1998; 275: H1040-H1045.
8. Wannamethee S G, Lowe G D O, Shaper A G, Rumley A, Lennon L, Whincup P H. Associations between cigarette smoking, pipe/cigar smoking, and smoking cessation, and haemostatic and inflammatory markers for cardiovascular disease. Eur Heart J. 2005; 26: 1765-1773.
9. Yanbaeva D G, Dentener M A, Creutzberg E C, Wesseling G, Wouters E F. Systemic effects of smoking. Chest. 2007; 131: 1557-66.
10. Heitzer T, Just H, Munzel T. Antioxidant vitamin C improves endothelial dysfunction in chronic smokers. Circulation. 1996; 94: 6-9.
11. Barua R S, Ambrose J A, Srivastava S, deVoe M, Eales-Reynolds L-J. Reactive oxygen species are involved in smoking-induced dysfunction of nitric-oxide biosynthesis and upregulation of endothelial nitric oxide synthase. An in vitro demonstration in human coronary artery endothelial cells. Circulation. 2003; 107: 2342-2347.
12. Chen J, Goligorsky M S. Premature senescence of endothelial cells: Methusaleh's dilemma. Am J Physiol. 2006; 290: H1729-H173.
13. Ben-Porath I, Weinberg R A. The signals and pathways activating cellular senescence. Int J Biochem Cell Biol. 2005; 37: 961-976.
14. Wagner M, Hampel B, Bernhard D, Hala M, Zwerschke W, Jansen-Durr P. Replicative senescence of human endothelial cells in vitro involves G1 arrest, polyploidization and senescence-associated apoptosis. Exp Gerontol. 2001; 36: 1327-1347.
15. Benetos A, Okuda K, Lajem M, Kimura M, Thomas F, Skurnick J, Labat C, Bean K, Aviv S. Telomere length as an indicator of biological aging: the gender effect and relation with pulse pressure and pulse wave velocity. Hypertension. 2001; 37: 381-385.
16. Cohen R A. The role of nitric oxide and other endothelium-derived vasoactive substances in vascular disease. Prog Cardiovasc Dis. 1995; 38: 105-128.
17. Serrano A L, Andres V. Telomeres and cardiovascular disease: does size matter? Circ Res. 2004; 94: 575-584.
18. Allsopp R C, Chang E, Kashefi-Aazam M, Rogaev E I, Piatyszek E A, Shay J W, Harley C B. Telomere shortening in associated with cell division in vitro and in vivo. Exp Cell Res. 1995; 200: 194-220.
19. Toussaint O, Medrano E E, von Zglinicki T. Cellular and molecular mechanisms of stress-induced premature senescence (SIPS) of human diploid fibroblasts and melanocytes. Exp Gerontol. 2000; 35: 927-945.
20. Shi W, Haberland M E, Jien M L, Shih D M, Lusis A J. Endothelial responses to oxidized lipoproteins determine genetic susceptibility to atherosclerosis in mice. Circulation. 2000; 102: 75-81.
21. Thorin E, Shatos M A, Shreeve S M, Walters C L, Bevan J A. Human vascular endothelium heterogeneity. A comparative study of cerebral and peripheral cultured vascular endothelial cells. Stroke. 1997; 28: 375-381.
22. Dimri G P, Lee X, Basile G, Acosta M, ScottG, Roskelley C, Medrano E E, Linskens M, Rubelj I, Pereira-Smith O, Peacock M, Campisi J. A biomarker that identifies senescent human cells in culture and in aging skin in vivo. Proc Natl Acad Sci USA. 1995; 92: 9363-9367.
23. Wang P, Zhang Z, Ma X, Huang Y, Liu X, Tu P, Tong T. HDTIC-1 and HDTIC-2, two compounds extracted from Astragali Radix, delay replicative senescence of human diploid fibroblasts. Mech Ageing Dev. 2003; 124: 1025-1034.
24. Hatsuda S, Shoji T, Shinohara K, Kimoto K, Mori K, Fukumoto S, Koyama H, Emoto M, Nishizawa Y. Association between plasma angiopoietin-like 3 protein and arterial wall thickness in healthy subjects. J Vas Res. 2006; 44: 61-66.
25. Sun H, Zheng J, Chen S, Zeng C, Liu Z, Li L, Enhanced expression of ANGPTL2 in the microvascular lesions of diabetic glomerulopathy. Nephron Exp Nephrol. 2007; 105: e117-e123.
26. Galbiati F, Volonte D, Liu J, Capozza F, Frank P G, Zhu L, Pestell R G, Lisanti M P. Caveolin-1 expression negatively regulates cell cycle progression by inducing $G_0/G_1$ arrest via p53/p21$^{WAF/CiP1}$-dependent mechanism. Mol Biol Cell. 2001; 12: 2229-44.
27. Herbig U, Jobling W A, Chen B P C, Chen D J, Sedivy J M. Telomere shortening triggers senescence of human cells through a pathway involving ATM, p53, and p21 but not p16$^{INK4a}$. Mol Cell. 2004; 14: 501-513.
28. Pandita T K. ATM function and telomere stability. Oncogene. 2002; 21: 611-618.
29. Miyauchi H, Minamino T, tateno K, Kunieda T, Toko H, Komuro I. Akt negatively regulates the in vitro lifespan of human endothelial cells via a p53/p21-dependent pathway. EMBO J. 2004; 23: 212-220.
30. Minamino T, Miyauchi H, Tateno K, Kunieda T, komuro I. Akt-induced cellular senescence. Implication for human disease. Cell cycle. 2004; 3: 449-451.
31. Morisada T, Kubota Y, Urano T, Suda T, Oike Y. Angiopoietins and angiopoietin-like proteins in angiogenesis. Endothelium. 2006; 13: 71-79.
32. Rytila P, Rehn T, Ilumets H, Rouhos A, Sovijarvi A, Myllarniemi M, Kinnula V L. Increased oxidative stress in asymptomatic current chronic smokers and GOLD stage 0 COPD. Respir Res. 2006; 7: 69-79.
33. Kanazawa H, Asai K, Nomura S. Vascular endothelial growth factor as a non-invasive marker of pulmonary vascular remodeling in patients with bronchitis-type of COPD. Respir Res. 2007; 8: 22-29.
34. Sharma S B, Dwivedi S, Prabhu K M, Singh G, Kumar N, Lal M K. Coronary risk variables in young asymptomatic smokers. Indian J Med Res. 2005; 122: 205-10.
35. Dietrich M, Block G, Hudes M, Morrow J D, Norkus E P, Traber M G, Cross C E, Packer L. Antioxidant supplementation decreases lipid peroxidation biomarker F2-isoprostanes in plasma of smokers. Cancer Epidelmiol, Biomarkers & Prevention. 2002; 11: 7-13.
36. Chen H J, Wu C F, Hong C L, Chang C. Urinary excretion of 3,N4-etheno-2'-deoxycytidine in humans as a biomarker of oxidative stress: association with cigarette smoking. Chem Res Toxicol. 2004; 17:896-903.
37. Asami S, Manabe H, Miyake J, Tsurudome Y, Hirano T, Yamaguchi R, Itoh H, Kasai H. Cigarette smoking induces an increase in oxidative DNA damage, 8-hydroxydeoxyguanosine, in a central site of the human lung. Carcinogenesis. 1997; 18:1763-6.
38. Kasahara Y, Tuder R M, Cool C D, Lynch D A, Flores S C, Voelkel N F. Endothelial cell death and decreased expression of vascular endothelial growth factor and vascular endothelial growth factor receptor 2 in emphysema. Am J Respir Crit Care Med. 2001; 163:737-44.
39. Conklin B S, Zhao W, Zhong D-S, Chen C. Nicotine and cotinine up-regulate vascular endothelial growth factor expression in endothelial cells. Am J Pathol. 2002; 160: 413-418.
40. Vivanco I, Sawyers C L. The phosphotidylinositol 3-kinase/Akt pathway in human cancer. Nat Rev Cancer. 2002; 2: 489-501.
41. Tsurutani J, Castillo S S, Brognard J, Granville C A, Zhang C, Gills J J, Sayyah J, Dennis P A. Tobacco components stimulate Akt-dependent proliferation and NFkB-dependent survival in lung cancer cells. Carcinogenesis. 2005; 26: 1182-1195.
42. Kim I, Kim J H, Moon S O, Kwak H J, Kim N G, Koh G Y. Angiopoietin-2 at high concentration can enhance endothelial cell survival through the phosphatidylinositol 3'-kinase/Akt signal transduction pathway. Oncogene. 2000; 19: 4549-4552.
43. Kubota Y, oike Y, Satoh S, Tabata Y, Niikura Y, Morisada T, Akao M, Urano T, Ito Y, Miyamoto T, Nagai N, Koh G Y, Watanabe S, Suda T. Cooperative interaction of angiopoietin-like proteins 1 and 2 in zebrafish vascular development. PNAS. 2005; 102: 13502-13507.
44. Tsuji T, Aoshiba K, Nagai A. Alveolar cell senescence in patients with pulmonary emphysema. Am J Respir Crit Care Med. 2006; 174:886-93.
45. Yokohori N, Aoshiba K, Nagai A. Increased levels of cell death and proliferation in alveolar wall cells in patients with pulmonary emphysema. Chest. 2004; 125: 626-632.
46. Valdes A M, Andrew T, Gardner J P, Kimura M, Oelsner E, Cherkas L F, Aviv A, Spector T D. Obesity, cigarette smoking, and telomere length in women. Lancet. 2005; 366: 662-664.
47. von Zglinicki T. Oxidative stress shortens telomeres. Trends Biochem Sci. 2002; 27: 339-344.
48. Andersen M R, Walker L R, Stender S. Reduced endothelial nitric oxide synthase activity and concentration in fetal umbilical veins from maternal cigarette smokers. Am J Obst and Gyn. 2004; 191: 346-351.
49. Hoshino S, Yoshida M, Inoue K, Yano Y, Yanagita M, Mawatari H, Yamane H, Kijima T, Kumagai T, Osaki T, Tachiba I, Kawase I. Cigarette smoke extract induces endothelial cell injury via JNK pathway. Biochem Biophys Res Commun. 2005; 329:58-63.
50. Michaud S E, Ménard C, Guy L-G, Gennaro G, Rivard A. Inhibition of hypoxia-induced angiogenesis by cigarette smoke exposure: impairment of the HIF-1 alpha/VEGF pathway. FASEB J. 2003; epub 2003 Apr. 22.

TABLE 1

Clinical profile of patients undergoing coronary artery bypass graft surgery.

| | Smokers (n = 26) | Former-smokers (n = 40) | Non-smokers (n = 20) |
|---|---|---|---|
| Sex (Male/Female) | 22/4 | 30/10 | 15/5 |
| Age (years) [range] | 56.2 ± 2.4 * [25-79] | 66.1 ± 1.6 [47-84] | 66.5 ± 2.1 [50-80] |
| BMI (kg/m$^2$) | 27.0 ± 0.9 | 28.7 ± 0.9 | 28.8 ± 1.1 |
| Glucose level (mM) | 6.5 ± 0.3 | 6.5 ± 0.2 | 6.7 ± 0.4 |
| LEVF (%) | 50.0 ± 2.4 | 51.8 ± 2.1 | 52.6 ± 2.7 |
| History of disease (years) [range] | 8.2 ± 2.6 [0.1-47] | 7.0 ± 1.2 [0.1-29] | 6.3 ± 1.9 [0.1-23] |
| Number of grafts | 2.7 ± 0.2 | 3.0 ± 0.1 | 2.9 ± 0.2 |
| Dyslipidemia (%) | 92 (23/25) | 85 (34/40) | 89.5 (17/19) |
| Hypertension (%) | 58 (14/24) | 75 (30/40) | 75 (15/20) |
| Diabetes (%) | 24 (6/25) | 30 (12/40) | 45 (9/20) |
| Family history CAD | 94 (16/17) | 85 (17/20) | 63.6 (7/11) |
| Renal failure (%) | 8 (2/25) | 17.5 (7/40) | 5 (1/20) |
| COPD (%) | 27 (7/26) | 23 (9/40) | 5 (1/20) |

* $p < 0.05$ versus non-smokers (ANOVA).

Patients were treated with similar medications including aspirin, angiotensin-converting enzyme inhibitors, β-blockers, calcium channels blockers, statins and nitrates.

TABLE 2

Initial gene expression in EC isolated from patients.

| mRNA | Non-smokers | Former-smokers | Smokers |
|---|---|---|---|
| Cox-2 | 0.531 ± 0.186 (12) | 0.738 ± 0.366 (14) | 0.617 ± 0.152 (13) |
| ANGPTL2 | 1.354 ± 0.461 (12) | 1.550 ± 0.306 (25) | 5.053 ± 1.944 (17) * |
| HIF-1-a | 11.295 ± 3.201 (11) | 7.325 ± 1.269 (24) | 7.684 ± 2.98 (15) |
| VEGF-A | 2.555 ± 0.452 (12) | 3.160 ± 0.646 (25) | 7.321 ± 1.083 (17) * |
| p53 | 1.224 ± 0.092 (5) | 1.368 ± 0.143 (15) | 2.414 ± 0.533 (12) * |
| p21 | 0.733 ± 0.130 (12) | 0.695 ± 0.132 (25) | 0.700 ± 0.173 (17) |
| p16 | 3.407 ± 0.612 (12) | 2.477 ± 0.445 (24) | 2.580 ± 0.364 (16) |
| ATM | 1.295 ± 0.393 (6) | 0.692 ± 0.098 (18) * | 0.689 ± 0.089 (14) * |
| Caveolin-1 | 0.446 ± 0.091 (8) | 0.691 ± 0.131 (19) | 3.666 ± 1.436 (14) * |

* $p < 0.05$ versus non-smokers (ANOVA).

TABLE 3

Simple linear regression between initial gene expression of ANGPTL2 and different parameters of EC in culture.

x: ANGPTL2

| y | $r^2$ | slope | intercept | p value |
|---|---|---|---|---|
| Days$_{X\text{-}Gal\,50\%}$ (n = 43) | 0.096 | 2.384 | 94.454 | 0.0410 * |
| ΣPDL (n = 43) | 0.337 | 1.316 | 10.566 | 0.0001 * |
| PDL$_{X\text{-}Gal\,50\%}$ (n = 44) | 0.221 | 0.726 | 10.819 | 0.0011 * |
| RFL initial (n = 37) | 0.006 | 27.578 | 8926.84 | 0.6378 |
| RFL final (n = 37) | 0.04 | 75.086 | 8405.91 | 0.2288 |
| ΔRFL/day (n = 37) | 0.158 | 2.066 | −13.433 | 0.0136 * |
| ΔRFL/ΣPDL (n = 35) | 0.166 | 8.304 | −67.565 | 0.0136 * |
| Initial Cox2 (n = 37) | 0.021 | −0.024 | 0.694 | 0.3862 |
| Initial VEGF (n = 52) | 0.126 | 0.286 | 3.622 | 0.0090 * |
| Initial p53 (n = 19) | 0.379 | 0.006 | 0.096 | 0.0039 * |
| Initial p21 (n = 52) | 0.046 | 0.027 | 0.644 | 0.1230 |
| Initial HIF-1 (n = 48) | 0.107 | 0.99 | 6.243 | 0.0215 * |
| Initial p16 (n = 50) | 0.003 | −0.023 | 2.76 | 0.6814 |

* $p < 0.05$ versus non-smokers (ANOVA).

TABLE 4

Effect of COPD on EC markers

| | Patients with COPD | Patients without COPD |
|---|---|---|
| ANGPTL2 mRNA | 7.557 ± 3.313 (9) * | 1.620 ± 0.323 (45) |
| VEGF-A mRNA | 7.325 ± 1.835 (9) * | 3.738 ± 0.493 (45) |
| p21 mRNA | 1.146 ± 0.263 (9) * | 0.617 ± 0.083 (45) |
| p53 mRNA | 3.963 ± 0.887 (9) * | 2.099 ± 0.224 (43) |
| HIF-1 mRNA | 9.726 ± 2.385 (8) | 8.036 ± 1.460 (42) |
| p16 mRNA | 1.973 ± 0.432 (9) | 2.880 ± 0.314 (43) |
| Cox-2 mRNA | 0.279 ± 0.150 (6) | 0.699 ± 0.172 (33) |
| Initial HNE level | 38.677 ± 15.742 (4) | 47.356 ± 16.378 (7) |
| pAkt/Akt activity | 1.020 ± 0.135 (9) | 1.065 ± 0.291 (19) |
| Caveolin-1 mRNA | 0.614 ± 0.218 (8) | 1.864 ± 0.638 (34) |
| ATM mRNA | 0.911 ± 0.100 (8) | 0.740 ± 0.101 (33) |

* $p < 0.05$ versus patients without COPD (ANOVA).

What is claimed is:

1. A method for assessing a physiological state of a human, said method comprising:
    obtaining from the human a biological sample, the biological sample comprising blood;
    measuring the expression of angiopoietin-like 2 protein in the blood; and
    assessing the physiological state of the human by comparing the measured quantity of the angiopoietin-like 2 protein to a predetermined quantity in normal subjects, wherein an increase in angiopoietin-like 2 protein quantity over the predetermined quantity indicates an abnormal physiological state;
    wherein the quantity of angiopoietin-like 2 protein in blood is at least about 2 times greater to about 5 times greater than the predetermined quantity in normal subjects.

2. A method for assessing a physiological state of vascular endothelial cells of a human, said method comprising:
    obtaining from the human a biological sample, said biological sample comprising blood;
    obtaining a measure of the quantity of angiopoietin-like 2 protein present in said biological sample; and
    assessing said physiological state of the vascular endothelial cells of the human by comparing the measured quantity of the angiopoietin-like 2 protein to a predetermined quantity in normal subjects, wherein an increase in angiopoietin-like 2 protein quantity over the predetermined quantity indicates an abnormal function in the vascular endothelial cells of the human;
wherein the quantity of angiopoietin-like 2 protein in said biological sample is at least about 2 times greater to about 5 times greater than the predetermined quantity in normal subjects.

3. The method as defined in claim 2, wherein said abnormal function is chronic inflammation.

4. The method as defined in claim 2, wherein said abnormal function is the creation of atherosclerotic lesions.

5. The method as defined in claim 2, wherein said abnormal function is an increased risk of developing atherosclerotic lesions.

6. The method as defined in claim 2, wherein said abnormal function is the presence of oxidative stress.

7. The method as defined in claim 2, wherein said abnormal function is abnormal cell proliferation.

8. The method as defined in claim 2, wherein the quantity of angiopoietin-like 2 proteins in the blood is at least about 4 times greater than the predetermined quantity in normal subjects.

9. The method as defined in claim 2, wherein the quantity of angiopoietin-like 2 proteins in the blood is at least about 2 times greater than the predetermined quantity in normal subjects.

10. The method as defined in claim 2, wherein the quantity of angiopoietin-like 2 proteins in the blood is at least about 5 times greater than the predetermined quantity in normal subjects.

11. The method as defined in claim 1 wherein the quantity of angiopoietin-like 2 protein in the blood is at least about 2 times greater than the predetermined quantity in normal subjects.

12. The method as defined in claim 1 wherein the quantity of angiopoietin-like 2 protein in the blood is at least about 5 times greater than the predetermined quantity in normal subjects.

13. A method as defined in claim 1 wherein said abnormal physiological state is oxidative stress.

14. A method as defined in claim 1 wherein said abnormal physiological state is abnormal cell proliferation.

15. A method as defined in claim 1 wherein said abnormal physiological state is chronic inflammation.

16. A method as defined in claim 1 wherein said abnormal physiological state is atherosclerosis.

* * * * *

SEQUENCE LISTING

<160> NUMBER OF SEQ ID NOS: 20

<210> SEQ ID NO 1
<211> LENGTH: 18
<212> TYPE: DNA
<213> ORGANISM: Artificial
<220> FEATURE:
<223> OTHER INFORMATION: primer

<400> SEQUENCE: 1
tggcgctcag ccatacag                                                 18

<210> SEQ ID NO 2
<211> LENGTH: 26
<212> TYPE: DNA
<213> ORGANISM: Artificial
<220> FEATURE:

```
<223> OTHER INFORMATION: primer

<400> SEQUENCE: 2
ggtacaatcg cacttatact ggtcaa                                        26

<210> SEQ ID NO 3
<211> LENGTH: 26
<212> TYPE: DNA
<213> ORGANISM: Artificial
<220> FEATURE:
<223> OTHER INFORMATION: primer

<400> SEQUENCE: 3
catcatcacc atatagagat actcaa                                        26

<210> SEQ ID NO 4
<211> LENGTH: 23
<212> TYPE: DNA
<213> ORGANISM: Artificial
<220> FEATURE:
<223> OTHER INFORMATION: primer

<400> SEQUENCE: 4
tctgagcatt ctgcaaagct agt                                           23

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
tgaggttggc tctgactgta                                               20

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
ttctcttcct ctgtgcgccg                                               20

<210> SEQ ID NO 7
<211> LENGTH: 20
<212> TYPE: DNA
<213> ORGANISM: Artificial
<220> FEATURE:
<223> OTHER INFORMATION: primer

<400> SEQUENCE: 7
ggacctgtca ctgtcttgta                                               20

<210> SEQ ID NO 8
<211> LENGTH: 21
<212> TYPE: DNA
<213> ORGANISM: Artificial
<220> FEATURE:
<223> OTHER INFORMATION: primer

<400> SEQUENCE: 8
cctcttggag aagatcagcc g                                             21

<210> SEQ ID NO 9
```

-continued

```
<211> LENGTH: 19
<212> TYPE: DNA
<213> ORGANISM: Artificial
<220> FEATURE:
<223> OTHER INFORMATION: primer

<400> SEQUENCE: 9
catagatgcc gcggaaggt                                                 19

<210> SEQ ID NO 10
<211> LENGTH: 20
<212> TYPE: DNA
<213> ORGANISM: Artificial
<220> FEATURE:
<223> OTHER INFORMATION: primer

<400> SEQUENCE: 10
tgtaggacct tcggtgactg                                                20

<210> SEQ ID NO 11
<211> LENGTH: 19
<212> TYPE: DNA
<213> ORGANISM: Artificial
<220> FEATURE:
<223> OTHER INFORMATION: primer

<400> SEQUENCE: 11
gcaatgcggg tgactcctt                                                 19

<210> SEQ ID NO 12
<211> LENGTH: 17
<212> TYPE: DNA
<213> ORGANISM: Artificial
<220> FEATURE:
<223> OTHER INFORMATION: primer

<400> SEQUENCE: 12
taccaggacg gagtcta                                                   17

<210> SEQ ID NO 13
<211> LENGTH: 20
<212> TYPE: DNA
<213> ORGANISM: Artificial
<220> FEATURE:
<223> OTHER INFORMATION: primer

<400> SEQUENCE: 13
gagggcagaa tcatcacgaa                                                20

<210> SEQ ID NO 14
<211> LENGTH: 20
<212> TYPE: DNA
<213> ORGANISM: Artificial
<220> FEATURE:
<223> OTHER INFORMATION: primer

<400> SEQUENCE: 14
aggagtccaa catcaccatg                                                20

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15
```

```
gctgagcgag aagcaagtgt                                          20

<210> SEQ ID NO 16
<211> LENGTH: 20
<212> TYPE: DNA
<213> ORGANISM: Artificial
<220> FEATURE:
<223> OTHER INFORMATION: primer

<400> SEQUENCE: 16
tggtgaagct ggccttccaa                                          20

<210> SEQ ID NO 17
<211> LENGTH: 20
<212> TYPE: DNA
<213> ORGANISM: Artificial
<220> FEATURE:
<223> OTHER INFORMATION: primer

<400> SEQUENCE: 17
ggcagctgat attcggagga                                          20

<210> SEQ ID NO 18
<211> LENGTH: 20
<212> TYPE: DNA
<213> ORGANISM: Artificial
<220> FEATURE:
<223> OTHER INFORMATION: primer

<400> SEQUENCE: 18
catcttggtc acgacgatac                                          20

<210> SEQ ID NO 19
<211> LENGTH: 20
<212> TYPE: DNA
<213> ORGANISM: Artificial
<220> FEATURE:
<223> OTHER INFORMATION: primer

<400> SEQUENCE: 19
tgaaggtcgg agtcaacgga                                          20

<210> SEQ ID NO 20
<211> LENGTH: 20
<212> TYPE: DNA
<213> ORGANISM: Artificial
<220> FEATURE:
<223> OTHER INFORMATION: primer

<400> SEQUENCE: 20
cattgatgac aagcttcccg                                          20
```